US009943698B2

(12) United States Patent
Chase et al.

(10) Patent No.: US 9,943,698 B2
(45) Date of Patent: Apr. 17, 2018

(54) COGNITIVE ENHANCEMENT USING FEEDBACK

(71) Applicants: Charles J. Chase, Lancaster, CA (US); Gerold Yonas, Albuquerque, NM (US)

(72) Inventors: Charles J. Chase, Lancaster, CA (US); Gerold Yonas, Albuquerque, NM (US)

(73) Assignee: Lockheed Martin Corporation, Bethesda, MD (US)

( * ) Notice: Subject to any disclaimer, the term of this patent is extended or adjusted under 35 U.S.C. 154(b) by 519 days.

(21) Appl. No.: 14/258,631

(22) Filed: Apr. 22, 2014

(65) Prior Publication Data
US 2015/0297108 A1    Oct. 22, 2015

(51) Int. Cl.
| | | |
|---|---|---|
| *A61B 5/0482* | (2006.01) | |
| *A61N 5/06* | (2006.01) | |
| *G09B 5/00* | (2006.01) | |
| *A61N 2/00* | (2006.01) | |
| *A61N 1/36* | (2006.01) | |

(Continued)

(52) U.S. Cl.
CPC ............ *A61N 2/006* (2013.01); *A61B 5/0022* (2013.01); *A61B 5/048* (2013.01); *A61B 5/16* (2013.01); *A61M 21/00* (2013.01); *A61N 1/36014* (2013.01); *A61N 1/36025* (2013.01); *A61N 5/0622* (2013.01); *G09B 5/00* (2013.01);
(Continued)

(58) Field of Classification Search
CPC ........ G09B 5/00; A61N 5/0622; A61N 2/006; A61N 2005/0648; A61N 1/36025; A61B 5/16; A61B 2503/20; A61B 5/048; A61B 5/0022; A61B 5/6803; A61M 21/00

USPC ..................... 600/9–14; 434/236; 607/62, 88
See application file for complete search history.

(56) References Cited

U.S. PATENT DOCUMENTS

| 3,032,029 A | 5/1962 | Cunningham |
| 4,739,772 A | 4/1988 | Hokanson et al. |

(Continued)

FOREIGN PATENT DOCUMENTS

| WO | 2006052679 | 5/2006 |
| WO | 2008029001 | 3/2008 |

OTHER PUBLICATIONS

Database Fundamentals by Robert J. Robbins, John Hopkins University, pp. 1-31, 1994.*
European Patent Office, Communication, Extended European Search Report, Application No. 15164640.3-1652, dated Oct. 1, 2015, 7 pages.

(Continued)

*Primary Examiner* — Navin Natnithithadha
*Assistant Examiner* — Sunita Reddy
(74) *Attorney, Agent, or Firm* — Baker Botts L.L.P.

(57) ABSTRACT

In an embodiment, a method includes determining a target frequency corresponding to a target brain state and stimulating a brain of a user using feedback to attempt to achieve the target brain state in the user. The stimulating step may include measuring an electrical output of the brain of the user received from one or more sensors coupled to the user, determining a current frequency associated with the brain of the user based on the measured electrical output, and determining a difference between the current frequency and the target frequency. When the difference between the current frequency and the target frequency is greater than a predetermined amount, the method includes sending a signal to the brain of the user through one or more pathways. The signal may have a frequency operable to modify the current frequency associated with the brain of the user towards the target frequency.

17 Claims, 5 Drawing Sheets

(51) Int. Cl.
*A61B 5/048* (2006.01)
*A61M 21/00* (2006.01)
*A61B 5/16* (2006.01)
*A61B 5/00* (2006.01)

(52) U.S. Cl.
CPC ......... *A61B 5/6803* (2013.01); *A61B 2503/20* (2013.01); *A61N 2005/0648* (2013.01)

(56) References Cited

U.S. PATENT DOCUMENTS

| | | | |
|---|---|---|---|
| 5,036,858 | A | 8/1991 | Carter et al. |
| 5,123,899 | A | 6/1992 | Gall |
| 5,406,957 | A | 4/1995 | Tansey |
| 5,899,867 | A | 5/1999 | Collura |
| 6,230,049 | B1 | 5/2001 | Fischell et al. |
| 6,488,617 | B1 * | 12/2002 | Katz ............... A61B 5/0482 600/26 |
| 6,549,804 | B1 | 4/2003 | Osorio et al. |
| 6,626,676 | B2 | 9/2003 | Freer |
| 6,996,261 | B2 | 2/2006 | deCharms |
| 7,751,878 | B1 | 7/2010 | Merkle et al. |
| 7,830,249 | B2 | 11/2010 | Dorneich et al. |
| 8,565,883 | B2 | 10/2013 | Lozano |
| 8,606,361 | B2 | 12/2013 | Gliner et al. |
| 2002/0103512 | A1 * | 8/2002 | Echauz ............ A61B 5/0482 607/9 |
| 2003/0153841 | A1 | 8/2003 | Kilborn |
| 2005/0159671 | A1 | 7/2005 | Sneddon |
| 2006/0293608 | A1 * | 12/2006 | Rothman ........... A61B 5/4812 600/545 |
| 2007/0142874 | A1 * | 6/2007 | John ............... A61N 1/3605 607/45 |
| 2009/0023977 | A1 * | 1/2009 | Sperling ........... A61M 21/00 600/27 |
| 2009/0099623 | A1 * | 4/2009 | Bentwich .......... A61N 1/36025 607/45 |
| 2012/0221075 | A1 * | 8/2012 | Bentwich .......... A61B 5/0476 607/45 |
| 2012/0289869 | A1 | 11/2012 | Tyler |
| 2012/0296390 | A1 | 11/2012 | Nakashima et al. |
| 2012/0319869 | A1 | 12/2012 | Dorfmann et al. |
| 2013/0030241 | A1 | 1/2013 | Smith |
| 2013/0245422 | A1 | 9/2013 | D'arcy et al. |
| 2015/0351655 | A1 * | 12/2015 | Coleman .......... A61B 5/0482 600/301 |

OTHER PUBLICATIONS

Zaehle, T., et al., "Transcranial Alternating Current Stimulation Enhances Individual Alpha Activity in Human EEG," PLoS One, http://www.plosone.org/article/info%3Adoi%2F10.1371%2Fjournal.pone.0013766, Published Nov. 1, 2010, 8 pages, Printed: Apr. 18, 2014.

Peter Goadsby, MD, PhD, "New therapy based on magnetic stimulation shows promise for non-drug treatment for migraine," http://www.ucsf.edu/news/2009/04/4229/new-therapy-based-magnetic-stimulation-shows- . . . , Posted by: Lauren Hammit on Apr. 29, 2009, 2 pages, Printed: Apr. 18, 2014.

Marshall, L., et al., "Transcranial Direct Current Stimulation during Sleep Improves Declarative Memory," *The Journal of Neuroscience*, Nov. 3, 2004—24(44):9985-9992, © 2004 Society for Neuroscience, 0270-6575/04/249985-08, 8 pages.

Walsh, J.K., Ph.D., "Enhancement of Slow Wave Sleep: Implications for Insomnia," *JCSM Journal of Clinical Sleep Medicine*, Supplement to vol. 5, No. 2, 2009, 6 pages, Apr. 15, 2009.

Hughes, David, "Darpa Pursues Neuroscience to Enhance Analyst, Soldier Performance," *Aviation Week* ô, http://www.freepublic.com/focus/f-news/1961770/posts, Posted on Tuesday, Jan. 29, 2008 by BGHater, 3 pages, Printed Apr. 18, 2014.

Zaghi, S., et al., "Noninvasive Brain Stimulation with Low-Intensity Electrical Currents: Putative Mechanisms of Action for Direct and Alternating Current Stimulation," *Neuroscientist OnlineFirst*, doi:10.1177/1073858409336227, The Neuroscientist vol. XX; No. XX, Month XXXX xx-xx, © 2009, http://nro.sagepub.com, 24 pages, Published Dec. 29, 2009.

Anastassiou, C.A., et al., "Ephaptic coupling of cortical neurons," *Nature Neuroscience*, Computation and Systems, vol. 14, No. 2, Feb. 2011, 8 pages, © 2011 Nature America, Inc. Printed Feb. 2011.

Nitsche, M.A., et al., "Treatment of depression with transcranial direct current stimulation (tDCS): A Review," *Experimental Neurology*, Article history: Revised Mar. 22, 2009, Accepted Mar. 26, 2009, Available online: Apr. 5, 2009, © 2009 Elsevier Inc.

Berenyl, A., et al., "Closed-Loop Control of Epilepsy by Transcranial Electrical Stimulation," *Science* vol. 337, Aug. 10, 2012, downloaded from www.sciencemag.org on Apr. 18, 2014.

Krakow, B., "Sleep Disorders Co-Morbidity Theory: A Novel Approach to PTSD Prevention and Treatment," http://www.podcastalley.com/podcast_details.php?pod_id=71253, Neuroscience for National Security Conference: Part 7, Mon, May 24, 2010, Podcast Size: 10.0 MB.

* cited by examiner

COGNITIVE ENHANCEMENT USING FEEDBACK

TECHNICAL FIELD

This disclosure generally relates to cognitive enhancement, and more particularly to cognitive enhancement using feedback.

BACKGROUND

Many professions involve tasks that cause fatigue, drowsiness, overload, and distraction, which negatively impact a worker's performance. Enhancement of cognitive function may address those negative effects, thereby increasing worker efficiency and reducing manpower costs. Additionally, cognitive enhancement may improve mental health, sleeping, learning, and training.

BRIEF DESCRIPTION OF THE DRAWINGS

For a more complete understanding of the present disclosure and for further features and advantages thereof, reference is now made to the following description taken in conjunction with the accompanying drawings, in which.

DETAILED DESCRIPTION

Figure 1:
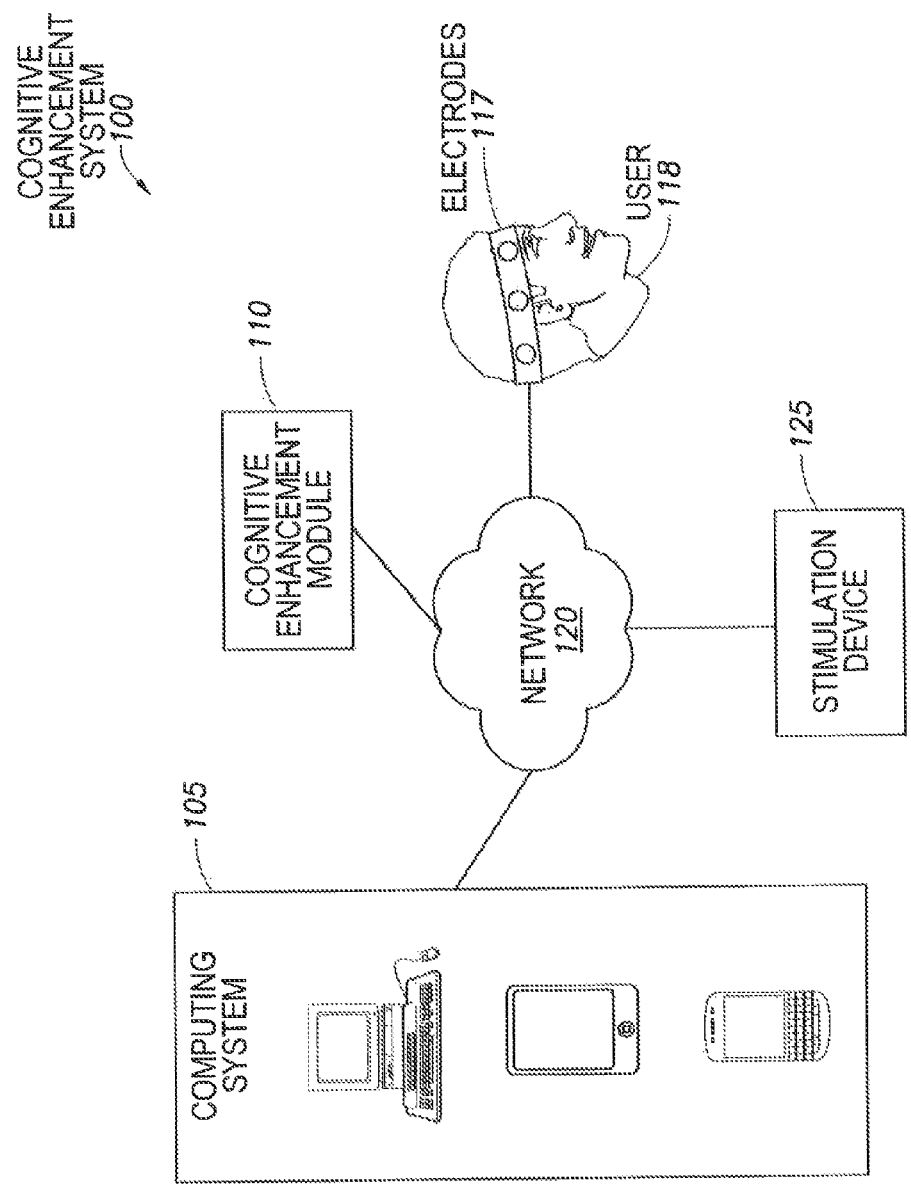
FIG. 1 is a network diagram illustrating an example cognitive enhancement system, according to certain embodiments of the present disclosure.

Professionals are often faced with demanding tasks. For example, during missions, a pilot must remain alert and focused for many hours. However, there may be long periods of boredom punctuated by times of intense focus. This uneven distribution of cognitive work can lead to periods of relaxed vigilance or cognitive overload, both of which can have a negative impact on mission performance. As another example, an intelligence analyst sits and analyzes pictures and other information for hours at a time. As a result, the analyst's alertness may be reduced. Cognitive enhancement through controlling the entrainment of brain waves can improve cognitive function thereby improving mission performance. Additionally, using a feedback loop may allow for active modification of a device-generated input signal in response to the brain's output signal. Moreover, a feedback loop may allow for real-time adjustments to govern how fast or slow a user's brain reaches a target brain state.

Accordingly, aspects of the present disclosure include a method that, in one embodiment, determines a target frequency corresponding to a target brain state and stimulates a brain of a user using feedback to achieve the target brain state in the user. Stimulating the brain of the user may include measuring an electrical output of the brain of the user received from one or more sensors coupled to the user, determining a current frequency associated with the brain of the user based on the measured electrical output, and determining a difference between the current frequency associated with the brain of the user and the target frequency. When the difference between the current frequency and the target frequency is greater than a predetermined amount, the method may include sending a signal to the brain of the user through one or more pathways, the signal having a frequency operable to modify the current frequency associated with the brain of the user towards the target frequency. The method may include repeating the measuring step, determining steps, and sending step one or more times.

Cognitive enhancement of the present disclosure may provide numerous advantages. As one example, cognitive enhancement module 110 provides for the use of feedback to make real-time adjustments to cognitive enhancement. As another example, cognitive enhancement module 110 may allow for increased accuracy in measurements of the electrical output of a user's brain through the use of encoded signaling and filtering. As yet another example, cognitive enhancement module 110 may provide a convenient and cost-effective cognitive enhancement system 100 that requires little overhead. As still yet another example, cognitive enhancement module 110 may provide for the treatment of numerous neurological disorders through cancelation of undesirable signals. As another example, cognitive enhancement module 110 provides for multiple excitation pathways so that a user may select the most effective pathway. As another example, cognitive enhancement module 110 may be customized to the particular user of cognitive enhancement system 100. As another example, cognitive enhancement module 110 provides a non-invasive cognitive stimulation thereby reducing or eliminating recovery times. As another example, cognitive enhancement module 110 may allow for control of frequency, amplitude, waveform, and location of the signals sent to the brain of user 118.

Figure 2:
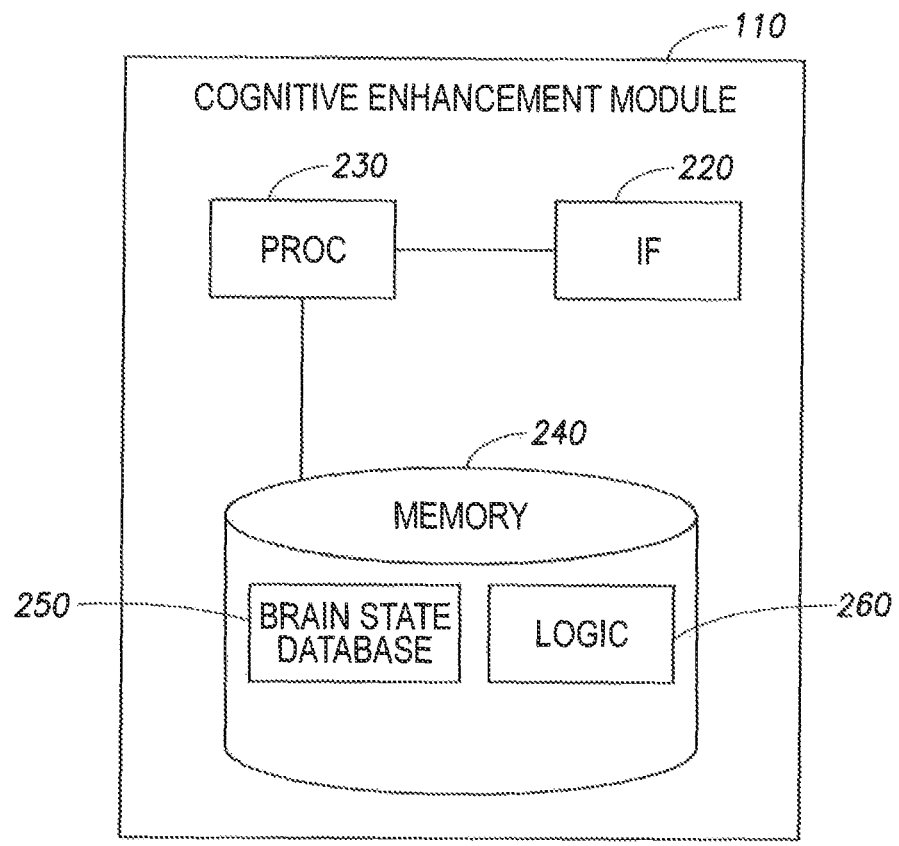
FIG. 2 is a diagram illustrating an example cognitive enhancement module used in the cognitive enhancement system of FIG. 1, according to certain embodiments of the present disclosure.
Figure 3:
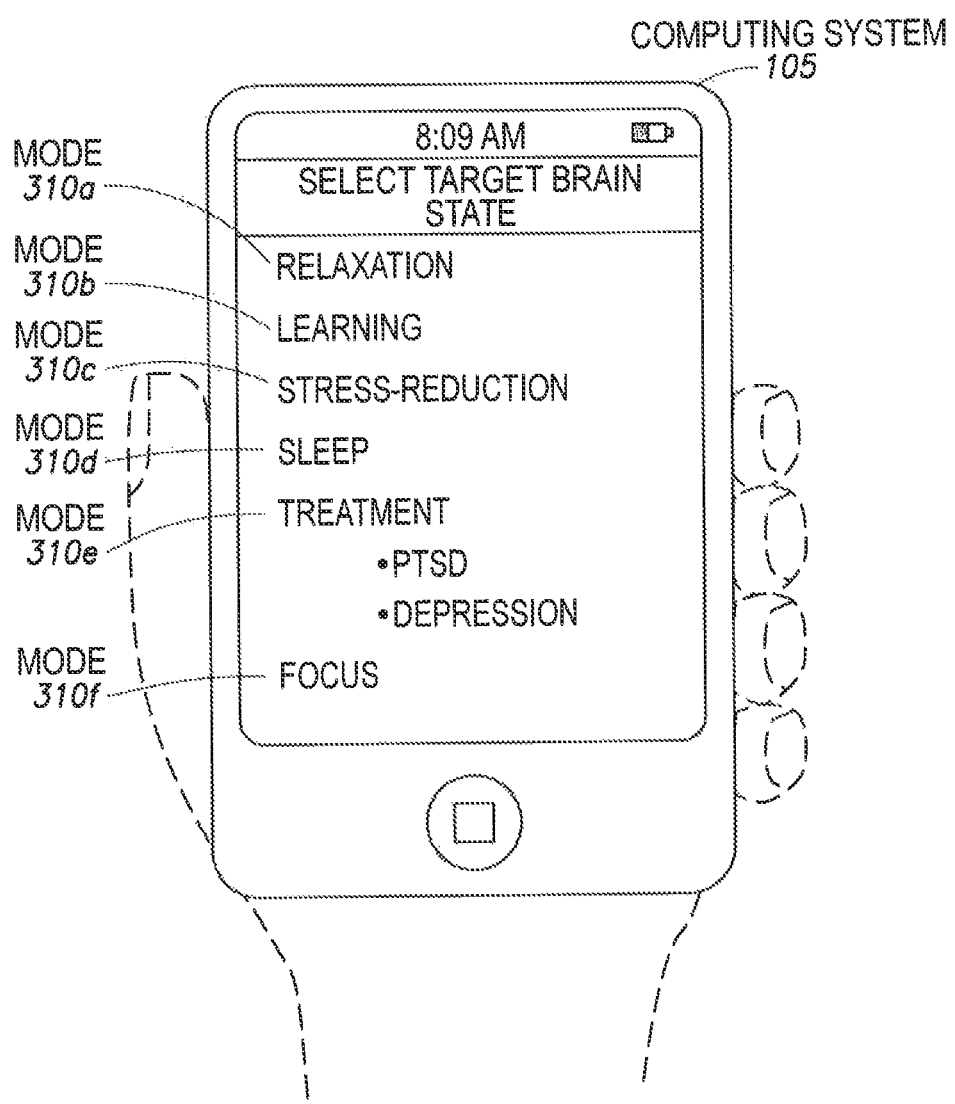
FIG. 3 is an example computing system used in the cognitive enhancement system of FIG. 1, according to certain embodiments of the present disclosure.
Figure 4A:
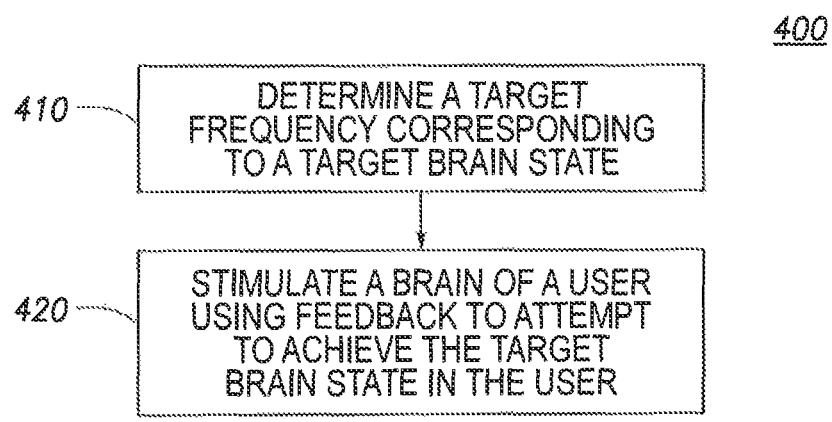
FIG. 4A is a flow chart illustrating an example method of cognitive enhancement using feedback, according to certain embodiments of the present disclosure.
Figure 4B:
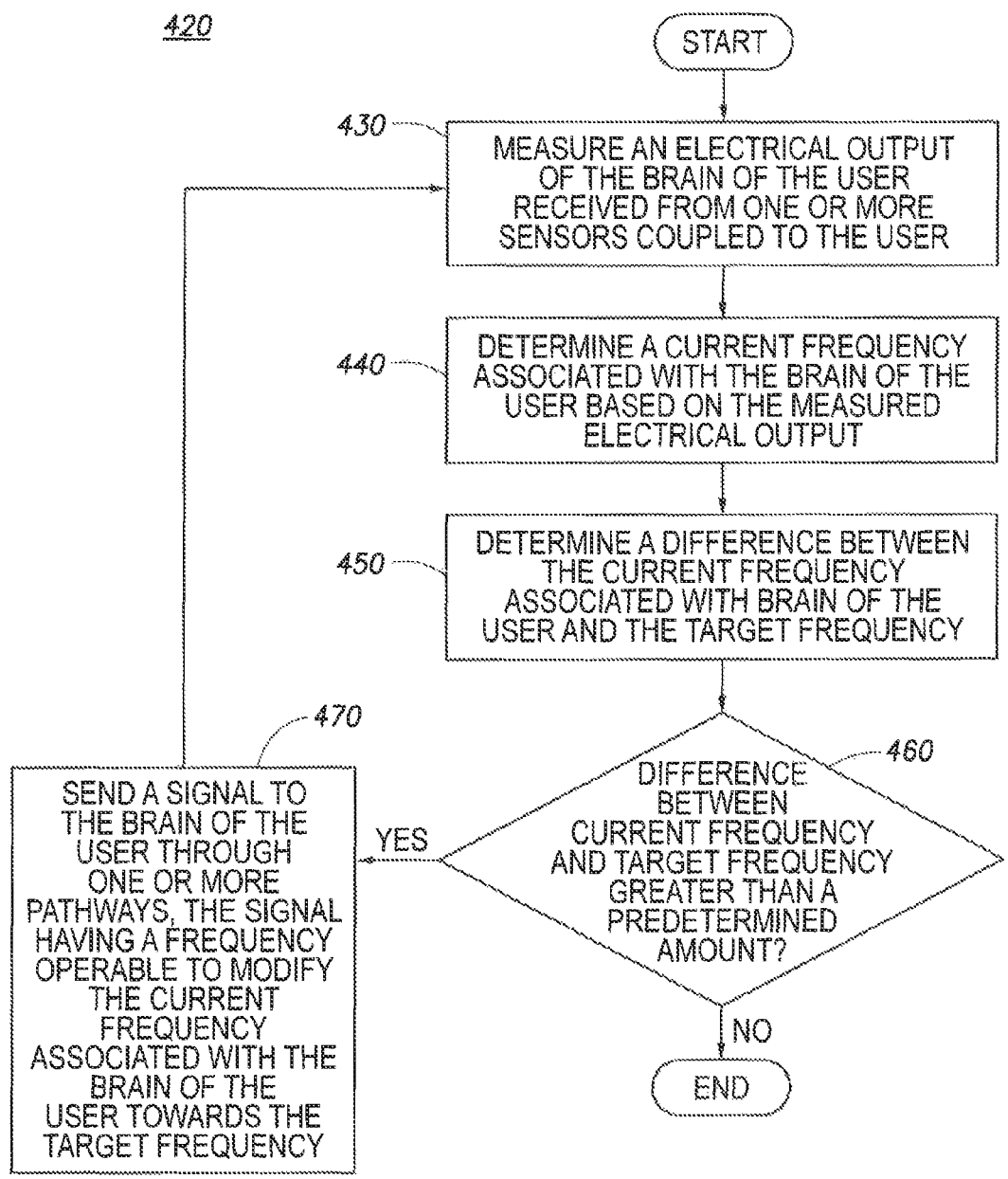
FIG. 4B is a flow chart illustrating an example method for the step of stimulating a brain of a user using feedback to achieve the target brain state in the user introduced in FIG. 4A, according to certain embodiments of the present disclosure.

Additional details are discussed in FIGS. 1 through 4B. FIG. 1 illustrates an example cognitive enhancement system 100. FIGS. 2 and 3 show an example cognitive enhancement module 110 and an example computing system 105, respectively, for use in the cognitive enhancement system 100 of FIG. 1. FIG. 4A shows an example method of cognitive enhancement using feedback, while FIG. 4B shows an example method for the step of stimulating a brain of a user using feedback to attempt to achieve the target brain state in the user introduced in FIG. 4A.

FIG. 1 illustrates cognitive enhancement system 100, according to certain embodiments of the present disclosure. Cognitive enhancement system 100 may provide for the enhancement of brainwaves to achieve a desired brain state in an embodiment. Cognitive enhancement system 100 may also provide for cancelation of undesirable brainwaves to improve cognitive functioning in some embodiments. Cognitive enhancement system 100 may include computing system 105, cognitive enhancement module 110, electrodes 117, user 118, network 120, and stimulation device 125 in an embodiment.

Computing system 105 may be any computing system configured to operate within cognitive enhancement system 100. For example, computing system 105 may be a tablet, a smartphone, a laptop, a personal computer, or any other device configured to communicate, process, and/or store information in cognitive enhancement system 100. Computing system 105 may also include a user interface, such as a display, a touchscreen, a microphone, a keypad, or other appropriate terminal equipment through which user 118, or another user, may operate cognitive enhancement system 100.

Cognitive enhancement module 110 may be any component configured to determine a target frequency of a target brain state and stimulate the brain of user 118 using feedback to attempt to achieve the target brain state. Cognitive enhancement module 110 may be connected to computing system 105, stimulation device 125, and electrodes 117 through network 120 in some embodiments. For example, cognitive enhancement module 110 may be software located on a remote server. Cognitive enhancement module 110 may be included within computing system 105 in other embodiments. For example, cognitive enhancement module 110 may be software installed on computing system 105. Cognitive enhancement module 110 may include a server, a remote server, a host computer, or any other suitable component in some embodiments. Although illustrated as a single module, in the case of a group of users 118, there may be multiple cognitive enhancement modules 110 with each module corresponding to a member of the group in certain embodiments. In that scenario, each cognitive enhancement module 110 may be communicatively coupled through network 120. In other embodiments, there may be a single cognitive enhancement module 110 remotely located that processes data and sends signals through network 120 to each member of the group. In some embodiments, the coupling of cognitive enhancement modules 110 in a group scenario may allow for sharing of cognitive enhancement. For example, if the cognitive enhancement module 110 associated with one member of the group receives an indication of brain waves associated with increased alertness, cognitive enhancement module 110 may be programmed to provide signals to increase alertness of other members of the group.

Electrodes 117 may be any type of electrode configured to sense electrical output of a brain in an embodiment. For example, electrodes 117 may include one or more sense electrodes. In some embodiments, electrodes 117 may include electrodes configured to provide electrical stimulation to the brain of user 118. For example, electrodes 117 may include one or more drive electrodes for stimulating the brain of user 118. Electrodes 117 may be configured to sense time-dependent electrical oscillations of the brain waves of user 118, which may be used to measure the frequency, waveform, location, amplitude, and magnitude of the oscillations. These oscillations can be related to various cognitive functions, including sleeping, learning, focusing, meditating, or any other cognitive function. Electrodes 117 may use the electroencephalography or magnetoencephalography techniques in certain embodiments. Electrodes 117 may include any number of electrodes. For example, a single electrode may be coupled to user 118. As another example, two or more electrodes 117 may be coupled to user 118. Electrodes 117 may be affixed or mounted to any apparatus configured to hold electrodes 117 in an embodiment. For example, electrodes 117 may be affixed to a hat or a headset that user 118 may wear. Electrodes 117 may be connected to computing system 105, cognitive enhancement module 110, and stimulation device 125 either directly or through network 120. In the scenario of a group of users 118, electrodes 117 may be of to each member of the group. In that scenario, each member of the group's electrodes 117 may be communicatively coupled to each other member of the group's electrodes through network 120.

User 118 may be a single person or a group of people. For example, user 118 may include a military brigade. As another example, user 118 may be a group of intelligence analysts. User 118 may also include an operator of cognitive enhancement system 100.

Network 120 may be any suitable network operable to facilitate communication between the components of cognitive enhancement system 100, such as computing system 105, cognitive enhancement module 110, electrodes 117, and stimulation device 125. Network 120 may include any interconnecting system capable of transmitting electrical, audio, video, light, data, messages, signals or any combination of the preceding. Network 120 may include all or a portion of a public switched telephone network (PSTN), a public or private data network, a local area network (LAN), a metropolitan area network (MAN), a wide area network (WAN), a local, regional, or global communication or computer network, such as the Internet, a wireline or wireless network, an enterprise intranet, or any other suitable communication link, including combinations thereof, operable to facilitate communication between the components.

Stimulation device 125 may be used to provide signals to the brain of user 118 in certain embodiments. Those signals may cause neurons in the brain of user 118 to "fire" at a target frequency. That is, the stimulation signal adjusts a brain wave to be in synchrony with the stimulation signal, which may cause the stimulation signal and the brain wave to become coupled together thereby achieving a desired waveform. Stimulation device 125 may be any device configured to provide signals at a certain frequency to the brain of user 118. For example, stimulation device 125 may be a trans-cranial brain stimulator, such as a trans-cranial alternating current stimulator, a trans-cranial magnetic stimulator, or a trans-cranial direct current stimulator. As another example, stimulation device 125 may be one or more drive electrodes. As yet another example, stimulation device 125 may be any device configured to provide a light signal through the ear or eye of user 118, such as a device with fiber optics or a pair of glasses with a display. As still yet another example, stimulation device 125 may be any device configured to provide an audible signal into an ear of user 118, such as a pair of headphones coupled to a sound-producing device. In some embodiments, stimulation device 125 may send signals through network 120. For example, stimulation device 125 may send an electrical signal over a wired or wireless connection of network 120 to electrodes 117. In other embodiments, stimulation device 125 may directly provide signals to the brain of user 118. For example, stimulation device 125 may provide a light signal directly through an ear or an eye of user 118. Although illustrated as a single stimulation device 125, cognitive enhancement system may include multiple stimulation devices 125 communicatively coupled together through network 120. For example, in the case of a group of users 118, there may be a corresponding stimulation device 125 coupled to each member of the group. Stimulation device 125 may be combined with computing system 105 or cognitive enhancement module 110 in certain embodiments.

As an example embodiment of operation, user 118 or an operator of cognitive enhancement system 100 may select a target brain state for a brain of user 118 using computing system 105 and cognitive enhancement module 110. Electrodes 117 may measure an output signal of the brain of user 118 and provide a signal to computing system 105 and cognitive enhancement module 110. Cognitive enhancement module 110 may analyze the received signal and determine a current frequency associated with the brain of user 118 based on the measured electrical output of the received signal. Cognitive enhancement module 110 may then determine a difference between the current frequency associated with the brain of user 118 and a target frequency associated with the target brain state. If the difference between the current frequency and the target frequency is greater than a predetermined amount, cognitive enhancement module 110 may cause stimulation device 125 to send a signal to the brain of user 118. The signal that stimulation device 125 provides to the brain of user 118 may have a frequency operable to modify the current frequency of the brain of user 118 towards the target frequency. The signal may adjust a brain wave to be in synchrony with the signal, which may cause the signal and the brain wave to become coupled together thereby achieving a desired waveform. Cognitive enhancement module 110 may then repeat this process one or more times until the target brain state is achieved.

FIG. 2 illustrates an example cognitive enhancement module 110 used in cognitive enhancement system 100 of FIG. 1, according to certain embodiments of the present disclosure. Cognitive enhancement module 110 is configured to stimulate the brain of user 118 using feedback to achieve a target brain state in user 118 in an embodiment. Cognitive enhancement module 110 is configured to treat neurological disorders by canceling undesirable brain waves in some embodiments. Cognitive enhancement module 110 includes interface 220, processor 230, and memory 240 in certain embodiments.

Interface 220 may be any suitable device configured to receive information from network 120, transmit information through network 120, perform processing of information, communicate with other devices, or any combination of the preceding. For example, interface 220 may receive a target brain state from computing system 105 through network 120. As another example, interface 220 may send a command through network 120 to stimulation device 125 thereby causing stimulation device 125 to provide a signal to user 118. In an embodiment, interface 220 represents any port or connection, real or virtual, including any suitable hardware and/or software, including protocol conversion and data processing capabilities, to communicate through a LAN, WAN, MAN, or other communication system that allows cognitive enhancement module 110 to exchange information with computing system 105, network 120, stimulation device 125, or any other component of cognitive enhancement system 100. Interface 220 may be communicatively coupled to processor 230 in certain embodiments.

Processor 230 communicatively couples with interface 220 and memory 240, and controls the operation and administration of cognitive enhancement module 110 by processing information received from interface 220 and memory 240 in an embodiment. Processor 230 includes any hardware and/or software that operates to control and process information. For example, processor 230 executes logic 260 to control the operation of cognitive enhancement module 110. Processor 230 may be a programmable logic device, a microcontroller, a microprocessor, any suitable processing device, or any suitable combination of the preceding.

Memory 240 stores, either permanently or temporarily, data, operational software, or other information for processor 230. Memory 240 includes any one or a combination of volatile or non-volatile local or remote devices suitable for storing information. For example, memory 240 may include RAM, ROM, magnetic storage devices, optical storage devices, or any other suitable information storage device or a combination of these devices. While illustrated as including particular modules, memory 240 may include any suitable information for use in the operation of cognitive enhancement module 110. In the illustrated embodiment, memory 240 includes brain state database 250 and logic 260.

Brain state database 250 may be any component configured to store frequencies and associated brain states. For example, brain state database 250 may be a Microsoft Access® database or a Microsoft Excel® database. Brain state database 250 may be a table associating a plurality of frequencies and corresponding target brain states in certain embodiments. As an example, brain state database 250 may have a cell for post-traumatic stress disorder ("PTSD") and an associated cell for a target brain frequency for improving a user's PTSD condition. As yet another example, brain state database 250 may have a cell for a target brain state of an expert and a corresponding frequency. Brain state database 250 may include target frequencies based on research that indicates that a target brain state corresponds to a particular target frequency in some embodiments. Brain state database 250 may include target frequencies customized to user 118 in an embodiment. For example, the frequencies at which the brain of user 118 is in a particular brain state may be measured and stored in brain state database 250.

Logic 260 generally refers to logic, rules, algorithms, code, tables, and/or other suitable instructions embodied in a computer-readable storage medium for performing the described functions and operations of cognitive enhancement module 110. For example, logic 260 facilitates the determination of a target frequency corresponding to a target brain state and stimulates the brain of user 118 using feedback to attempt to achieve the target brain state in user 118. In that example, logic 260 may measure an electrical output of the brain of user 118 received through interface 220 over network 120 from one or more sensors coupled to user 118. Logic 260 may determine a current frequency associated with the brain of user 118 based on the measured electrical output and determine a difference between the current frequency and the target frequency. When the difference between the current frequency and the target frequency is greater than a predetermined amount, logic 260 may cause stimulation device 125 to send a signal to the brain of user 118 through one or more pathways. The signal may have a frequency operable to modify the current frequency associated with the brain of user 118 towards or to the target frequency in certain embodiments.

FIG. 3 illustrates an example computing system 105 used in cognitive enhancement system 100 of FIG. 1, according to certain embodiments of the present disclosure. As noted above, computing system 105 may be a tablet, a smartphone, a laptop, a personal computer, or any other device configured to communicate, process, and/or store information in cognitive enhancement system 100 in an embodiment. In certain embodiments, computing system 105 may allow a user, such as user 118, to select a target brain state through the selection of various modes 310A-F within an application on computing system 105.

Modes 310A-F may correspond to any target brain state. For example, mode 310A may correspond to relaxation. As another example, mode 310B may correspond to a learning brain state. Each of modes 310A-F may be selectable by user 118 though a user input in an embodiment. For example, user 118 may touch, select, or swipe any of modes 310A-F to select a target brain state. In other embodiments, user 118 may provide a voice command to select one of modes 310A-F. Although described as being performed by user 118, selection of modes 310A-F may be performed by an operator of cognitive enhancement system 100, such as a doctor, in certain embodiments. Modes 310A-F may also include treatment mode 310E, which may display neurological disorders for which user 118 may receive treatment. For example, computing system 105 may display treatment mode 310E corresponding to PTSD, depression, epilepsy, or any other neurological disorder. Upon selection of one of modes 310A-F, computing system 105 may provide a signal to cognitive enhancement module 110 through network 120 in certain embodiments. In embodiments in which cognitive enhancement module 110 resides on computing system 105, the signal may be directly provided to cognitive enhancement module 110 without going through network 120. The signal may be indicative of the selection of user 118 in certain embodiments.

FIG. 4A illustrates an example method 400 of cognitive enhancement using feedback, according to certain embodiments of the present disclosure. Method 400 begins at step 410 where a target frequency corresponding to a target brain state may be determined. To determine a target frequency corresponding to a target brain state, cognitive enhancement module 110 may look up the target frequency in brain state database 250 associated with the target brain state in an embodiment. For example, if a user selects mode 310B using the example computing system 105 in FIG. 3, cognitive enhancement module 110 may search brain state database 250 for a target brain state of learning. When cognitive enhancement module 110 finds the target brain state of learning in brain state database 250, cognitive enhancement module 110 may retrieve the target frequency corresponding to the selected learning brain state.

At step 420, the brain of user 118 may be stimulated using feedback to attempt to achieve the target brain state in user 118. An example method of stimulating the brain of user 118 using feedback to attempt to achieve the target brain state in user 118 is illustrated in FIG. 4B and discussed below.

FIG. 4B illustrates an example method 420 for the step of stimulating the brain of user 118 using feedback to achieve the target brain state in user 118 introduced in FIG. 4A, according to certain embodiments of the present disclosure. At step 430, an electrical output of the brain of user 118 received from one or more sensors coupled to user 118 may be measured. The sensors may include electrodes 117 in certain embodiments. Electrodes 117 may sense electrical oscillations of the brain waves of user 118 in certain embodiments. Electrodes 117 may provide a signal associated with the sensed electrical oscillations to cognitive enhancement module 110, which may perform various measurements using the signal in some embodiments. Various characteristics of brain waves outputted through the brain of user 118 are measured in some embodiments. For example, the measured characteristics may include the wave location (i.e., location in the brain at which the brain wave occurred), frequency, and magnitude of the time-dependent electrical oscillations that are outputted from the brain of user 118. These oscillations indicate neural activity that can be related to certain functions of the brain.

At step 440, a current frequency associated with the brain of user 118 may be determined based on the measured electrical output. The current frequency may be the frequency at which neurons in the brain of user 118 "fire" in an embodiment. The current frequency of the time electrical oscillations may be measured using the electrical output received from one or more sensors coupled to user 118, such as electrodes 117, in certain embodiments.

At step 450, a difference between the current frequency associated with the brain of user 118 and the target frequency may be determined. In some embodiments, the determination may be made based on a subtraction between the current frequency and the target frequency. As noted above, the target frequency may be obtained from brain state database 250 in certain embodiments.

At step 460, the difference between the current frequency and the target frequency may be compared to a predetermined amount. The predetermined amount may be a threshold set by an operator of cognitive enhancement system 100 in certain embodiments. For example, an operator of cognitive enhancement system 100 may set the predetermined amount using an application on computing system 105. In other embodiments, user 118 may set the predetermined amount using computing system 105. The predetermined amount may also be hardcoded into logic 260 of cognitive enhancement module 110. For example, the predetermined amount may be a fixed amount that is not adjustable by user 118. When the difference between the current frequency and the target frequency is less than the predetermined amount, cognitive enhancement module 110 determines that the target brain state has been achieved, and method 420 ends. When the difference between the current frequency and the target frequency is greater than the predetermined amount, cognitive enhancement module 110 determines that the target brain state has not yet been achieved, and the method proceeds to step 470.

At step 470, a signal may be sent to the brain of user 118 through one or more pathways. The signal sent to the brain of user 118 may have a frequency operable to modify the current frequency associated with the brain of user 118 towards or to the target frequency in some embodiments. For example, if the target brain state is a learning state, which may have an associated target frequency of 5 Hz, and the current frequency of the brain of user 118 is 2 Hz, then the signal sent to the brain of user 118 may have a frequency of 3 Hz. In that example, the signal may modify the current frequency of 2 Hz towards the target frequency of 5 Hz. As another example, the signal may have a frequency of 10 Hz, which may be operable to modify the current frequency of 5 Hz to the target frequency of 10 Hz. In that example, user 118 may have its eyes open at 5 Hz. In some embodiments, the signal may be time synchronized with the electrical output of the brain in order to provide an in-phase, equal-magnitude signal having the same sign as the electrical output, which may increase the amplitude of the current frequency. In some embodiments, the signal may adjust a brain wave to be in synchrony with the stimulation signal, which may cause the stimulation signal and the brain wave to become coupled together thereby achieving a desired waveform.

The signal sent to the brain of user 118 may cancel undesirable brain waves in other embodiments. For example, if the brain of user 118 includes undesirable brain waves, cognitive enhancement module 110 may send a signal to the brain of user 118 that is 180 degrees out of phase with the undesirable brain waves. In that manner, the undesirable brain waves may be canceled. Cancelation of undesirable brain waves may be useful for treatment of neurological disorders. For example, if user 118 has PTSD, epilepsy, sleep deprivation, stress, boredom, or any other neurological disorder, the undesirable brain waves associated with each of those disorders may be canceled by sending a signal that is 180 degrees out of phase with the undesirable signal.

The signal sent to the brain of user 118 may be encoded in certain embodiments. Encoding the signal with a code identifying the signal may allow for an increase in the accuracy of the measurements of the brain of user 118 because the encoded signal can be filtered from the electrical output of the brain using the code. If the signal sent to the brain of user 118 is not filtered, the measurements of the electrical output of the brain may be distorted. As an example embodiment of operation, cognitive enhancement module 110 may modulate a signal sent to the brain of user 118 with a code identifying the signal. Electrodes 117 may sense an electrical output of the brain of user 118, which may include both the electrical oscillations of the brain and the encoded signal sent to the brain. Because electrodes 117 may sense both the electrical oscillations and the encoded signal sent to the brain, cognitive enhancement module 110 may filter the encoded signal from the total electrical output based on the code modulated onto the encoded signal. As a result, cognitive enhancement module 110 may perform more accurate measurements of the electrical oscillations of the brain of user 118.

The one or more pathways through which a signal is sent may be any excitation pathway configured to provide a signal to the brain of user 118 in certain embodiments. An electromagnetic pathway may be used in an embodiment. For example, the electromagnetic pathway may include trans-cranial alternating current stimulation or a trans-cranial magnetic stimulation. Another pathway may be a optical pathway, which provides an optical stimulation, in certain embodiments. For example, the optical stimulation may include a light signal sent through the ear of user 118. As another example, the optical stimulation may include a light signal sent through the eye of user 118. An audible pathway may be used in some embodiments. For example, an audible pathway may include a sound sent through the ear of user 118. In some embodiments in which an audible pathway is used, a sound may be sent at a different frequency into each ear of user 118 to entrain the brain of user 118 at a frequency that is the difference between the frequencies of the sounds. Multiple pathways may be used at once in certain embodiments. For example, both an electromagnetic pathway and an audible pathway may be used simultaneously. As another example, both an optical pathway through the eye and an optical pathway through the ear may be used simultaneously.

After sending the signal in step 470, method 420 may then proceed to step 430 where steps 430-470 are performed until the difference between the current frequency and the target frequency is less than the predetermined amount, at which point method 420 ends. Repetition of steps 430-470 provides cognitive enhancement module 110 with a feedback loop in certain embodiments. The feedback loop allows for real-time adjustments. The range of stimulation may be adjusted in certain embodiments. For example, if the current frequency is not progressing towards the target frequency fast enough, the frequency of the signal sent to the brain of user 118 may be adjusted to speed up the modification of the current frequency of the brain. Alternatively, if the current frequency is progressing towards the target frequency too fast, the frequency of the signal may be adjusted to slow down the modification of the current frequency. In some embodiments, user 118 may use the feedback loop to adjust the range of stimulation. In other embodiments, an operator of cognitive enhancement system 100 may use the feedback loop to adjust the range of stimulation.

As another use of feedback, the location of stimulation may be adjusted so as to direct the signal towards those regions of the brain responsible for generating a target brain state. For example, the signal sent to the brain of user 118 may be sent to a selected subset of electrodes 117 positioned at particular locations on the head of user 118. As another example, user 118 or an operator of cognitive enhancement system 100 may move the location of electrodes 117. By changing the location of electrodes 117, the area of the brain of user 118 that is stimulated is adjusted. In addition to frequency and location control using feedback, the amplitude and waveform of a signal may also be controlled in an embodiment.

As an example embodiment of operation, cognitive enhancement module 110 determines a target frequency corresponding to a target brain state. For example, cognitive enhancement module 110 may perform a search in brain state database 250 to determine the target frequency associated with a target brain state selected by user 118. Cognitive enhancement module 110 may stimulate the brain of user 118 using feedback to attempt to achieve the target brain state. To stimulate the brain of user 118, cognitive enhancement module 110 may measure an electrical output of the brain of user 118 received from one or more sensors coupled to user 118. For example, cognitive enhancement module 110 may receive a signal from electrodes 117 and measure various characteristics of the signal. Cognitive enhancement module 110 may determine a current frequency associated with the brain of user 118 based on the measured electrical output. For example, cognitive enhancement module 110 may calculate the current frequency using the measured electrical output. Cognitive enhancement module 110 may determine a difference between the current frequency and the target frequency. For example, cognitive enhancement module 110 may subtract the current frequency from the target frequency. When the difference between the current frequency and the target frequency is greater than a predetermined amount, cognitive enhancement module 110 may send a signal to the brain of user 118 through one or more pathways. The signal may have a frequency operable to modify the current frequency towards the target frequency. Cognitive enhancement module 110 may repeat the measuring, determining, and sending steps until the target brain state is achieved.

Cognitive enhancement module 110 provides numerous advantages. Cognitive enhancement module 110 may provide for the use of feedback to make real-time adjustments to cognitive enhancement in certain embodiments. Cognitive enhancement module 110 may allow for increased accuracy in measurements of the electrical output of a user's brain through use of encoded signaling and filtering in some embodiments. Cognitive enhancement module 110 may provide for a convenient and cost-effective cognitive enhancement system 100 that requires little overhead in some embodiments. Cognitive enhancement module 110 may provide for the treatment of numerous neurological disorders through use of cancelation of undesirable signals in certain embodiments. Cognitive enhancement module 110 may provide for multiple excitation pathways so that a user may select the most effective pathway in an embodiment. Cognitive enhancement module 110 may be customized to the particular user of cognitive enhancement system 100 in some embodiments. Cognitive enhancement module 110 may provide for a non-invasive cognitive stimulation thereby reducing or eliminating recovery times in an embodiment. As another example, cognitive enhancement module 110 may allow for control of frequency, amplitude, waveform, and location of the signals sent to the brain of user 118.

Although the present disclosure has been described with several embodiments, a myriad of changes, variations, alterations, transformations, and modifications may be suggested to one skilled in the art, and it is intended that the present disclosure encompass such changes, variations, alterations, transformations, and modifications.

What is claimed is:

1. A method, comprising:
   determining, by a processor, a target frequency corresponding to a target brain state; and
   stimulating, by the processor, a brain of a user using feedback to achieve the target brain state in the user by repeating the following one or more times:
      measuring an electrical output of the brain of the user received from one or more sensors coupled to the user;
      determining a current frequency associated with the brain of the user based on the measured electrical output;
      determining a difference between the current frequency associated with the brain of the user and the target frequency; and
      sending two or more signals to the brain of the user along two or more pathways using a plurality of distinct types of stimulation devices, wherein the sending of the two or more signals to the brain of the user is based upon a determination, by the processor, that the difference between the current frequency and the target frequency is greater than a predetermined amount, the two or more signals having a frequency operable to modify the current frequency associated with the brain of the user towards the target frequency, wherein the two or more pathways comprise a first optical pathway through an eye and a second optical pathway through an ear, wherein the plurality of distinct types of stimulation devices comprise an optical device and an audible device, wherein the two or more signals are simultaneously sent along the two or more pathways using the optical device and the audible device, to simultaneously provide stimulating signals to the brain of the user.

2. The method of claim 1, wherein one of the stimulation devices is an electromagnetic stimulator.

3. The method of claim 1, wherein one of the two or more pathways is an audible pathway.

4. The method of claim 1, wherein the target frequency is determined based on data received from a user device indicative of a user selection of the target brain state.

5. The method of claim 1, further comprising:
   encoding, using the processor, the two or more signals with a respective code each identifying a respective one or more of the two or more signals; and
   filtering, using the processor, the two or more signals from the electrical output of the brain of the user based on the code.

6. The method of claim 1, further comprising storing the target frequency in a database, the database comprising a plurality of frequencies each corresponding to a particular brain state.

7. A non-transitory, computer-readable medium comprising logic operable to:
   determine a target frequency corresponding to a target brain state; and
   stimulate a brain of a user using feedback to achieve the target brain state in the user by repeating the following one or more times:
      measure an electrical output of the brain of the user received from one or more sensors coupled to the user;
      determine a current frequency associated with the brain of the user based on the measured electrical output;
      determine a difference between the current frequency associated with the brain of the user and the target frequency; and
      send two or more signals to the brain of the user along two or more pathways using a plurality of distinct types of stimulation devices, wherein the two or more signals are sent to the brain of the user based upon a determination, by the processor, that the difference between the current frequency and the target frequency is greater than a predetermined amount, the two or more signals having a frequency operable to modify the current frequency associated with the brain of the user towards the target frequency, wherein the two or more pathways comprise a first optical pathway through an eye and a second optical pathway through an ear, wherein the plurality of distinct types of stimulation devices comprise an optical device and an audible device, wherein the two or more signals are simultaneously sent along the two or more pathways using the optical device and the audible device, to simultaneously provide stimulating signals to the brain of the user.

8. The computer-readable medium of claim 7, wherein one of the stimulation devices is an electromagnetic stimulator.

9. The computer-readable medium of claim 7, wherein one of the two or more pathways is an audible pathway.

10. The computer-readable medium of claim 7, wherein the target frequency is determined based on data received from a user device indicative of a user selection of the target brain state.

11. The computer-readable medium of claim 7, wherein the logic is further operable to:
    encode the two or more signals with a respective code each identifying a respective one or more of the two more signals; and
    filter the two more signals from the electrical output of the brain of the user based on the code.

12. The computer-readable medium of claim 7, wherein the logic is further operable to store the target in a database, the database comprising a plurality of frequencies each corresponding to a particular brain state.

13. A system, comprising:
    a memory;
    one or more processors communicatively coupled to the memory and operable to:
       determine a target frequency corresponding to a target brain state; and
       stimulate a brain of a user using feedback to achieve the target brain state in the user by repeating the following one or more times:
          measure an electrical output of the brain of the user received from one or more sensors coupled to the user;
          determine a current frequency associated with the brain of the user based on the measured electrical output;
          determine a difference between the current frequency associated with the brain of the user and the target frequency; and
          send two or more signals to the brain of the user along two or more pathways using a plurality of distinct types of stimulation devices, wherein the two or more signals are sent to the brain of the user based upon a determination, by the processor, that the difference between the current frequency and the target frequency is greater than a predetermined amount, the two or more signals having a frequency operable to modify the current frequency associated with the brain of the user towards the target frequency, wherein the two or more pathways comprise a first optical pathway through an eye and a second optical pathway through an ear, wherein the plurality of distinct types of stimulation devices comprise an optical device and an audible device, wherein the two or more signals are simultaneously sent along the two or more pathways using the optical device and the audible device, to simultaneously provide stimulating signals to the brain of the user.

14. The system of claim 13, wherein one of the stimulation devices is an electromagnetic stimulator.

15. The system of claim 13, wherein one of the two or more pathways is an audible pathway.

16. The system of claim 13, wherein the one or more processors are further operable to:
  encode the two or more signals with a respective code each identifying a respective one or more of the two or more signals; and
  filter the two or more signals from the electrical output of the brain of the user based on the code.

17. The system of claim 13, wherein the logic is further operable to store the target frequency in a database, the database comprising a plurality of frequencies each corresponding to a particular brain state.

* * * * *

UNITED STATES PATENT AND TRADEMARK OFFICE
CERTIFICATE OF CORRECTION

PATENT NO. : 9,943,698 B2
APPLICATION NO. : 14/258631
DATED : April 17, 2018
INVENTOR(S) : Charles J. Chase and Gerold Yonas Page 1 of 1

It is certified that error appears in the above-identified patent and that said Letters Patent is hereby corrected as shown below:

In the Claims

Column 12, Line 36: before "more signals; and" add "or".

Signed and Sealed this
Third Day of March, 2020

Andrei Iancu
*Director of the United States Patent and Trademark Office*